United States Patent [19]

Lisi

[11] Patent Number: 5,789,185
[45] Date of Patent: *Aug. 4, 1998

[54] SELECTIVE IMMUNOASSAY FOR IL-1β

[75] Inventor: Peter J. Lisi, Flemington, N.J.

[73] Assignee: Cistron Biotechnology, Inc., Pine Brook, N.J.

[ * ] Notice: The term of this patent shall not extend beyond the expiration date of Pat. No. 5,474,899.

[21] Appl. No.: 570,074

[22] Filed: Dec. 11, 1995

Related U.S. Application Data

[62] Division of Ser. No. 164,283, Dec. 7, 1993, Pat. No. 5,474,899, which is a continuation of Ser. No. 958,442, Oct. 6, 1992, abandoned, which is a continuation of Ser. No. 496,168, Mar. 19, 1990, abandoned, which is a continuation of Ser. No. 49,630, May 13, 1987, abandoned.

[51] Int. Cl.$^6$ .................... G01N 33/53; G01N 33/543
[52] U.S. Cl. .................... 435/7.92; 435/7.1; 435/7.9; 530/389.2; 530/387.1; 530/388.23; 530/389.1; 436/518
[58] Field of Search ............... 530/389.2, 387.1, 530/388.23, 389.1; 435/7.9, 7.1, 7.92; 436/518

[56] References Cited

U.S. PATENT DOCUMENTS

| | | |
|---|---|---|
| 4,134,792 | 1/1979 | Boguslaski et al. . |
| 4,376,110 | 3/1983 | David et al. . |
| 4,766,069 | 8/1988 | Auron et al. . |
| 4,772,685 | 9/1988 | Schmidt et al. ............ 530/326 |
| 4,935,343 | 6/1990 | Allison et al. . |
| 5,474,899 | 12/1995 | Lisi ............................ 435/7.1 |

FOREIGN PATENT DOCUMENTS 8801624   3/1988   WIPO .

OTHER PUBLICATIONS

Arend, W.P. et al. (1985) "Effects of Immune Complexes on Production by Human Monocytes of Interleukin 1 or an Interleukin 1 Inhibitor" The Journal of Immunology 134(6):3868–3874.

Auron, P.E. et al. (1985) "Human and Murine Interleukin 1 Possess Sequence and Structural Similarities" J. Mol. Cell Immunol. 2:169–177.

Auron, P.E. et al. (1984) "Nucleotide sequence of human monocyte interleukin 1 precursor cDNA" Proc. Natl. Acad. Sci. USA 81:7909–7912.

Beutler, B., A Cerami (1986) "Cachectin and tumour necrosis factor as two sides of the same biological coin" Nature 32:584–588.

Bevilacqua, M.P. et al. (1984) "Interleukin 1 (IL–1) Induces Biosynthesis and Cell Surface Expression of Procoagulant Activity in Human Vascular Endothelial Cells" J. Exp. Med. 160:618–623.

Conlon, P.J. (1983) "A Rapid Biologic Assay for the Detection of Interleukin 1" The Journal of Immunology 131(3):1280–1282.

Dayer, J.–M. et al. (1986) "Human Recombinant Interleukin–1 Stimulates Collagenase and Prostaglandin $E_2$ Production by Human Synovial Cells" J. Clin. Invest. 77:645–648.

Dejana, E. et al. (1983) "Prostacyclin Production by Human Endothelial and Bovine Smooth Muscle Cells in Culture: Effect of Repeated Stimulation with Arachidonic Acid, Thrombin and Ionophore A23187" Biochimica et Biophysica Acta. 750:261–267.

Dinarello, C.A. et al. (1983) "Role of Arachidonate Metabolism in the Immunoregulatory Function of Human Leukocytic Pyrogen/Lymphocyte–Activating Factor/Interleukin 1" The Journal of Immunology 130(2):890–895.

Dinarello, C.A. et al. (1986) "Multiple Biological Activities of Human Recombinant Interleukin 1" J. Clin. Invest. 77:1734–1739.

Dinarello, C.A. et al. (1986) "Tumor Necrosis Factor (Cachectin) is an Endogenous Pyrogen and Induces Production of Interleukin 1" J. Med. Chem. 163:1433–1450.

Fox, D.A. et la. (1986) "Regulation of the Alternative Pathway of T Cell Activation by Anti–T3 Monoclonal Antibody" The Journal of Immunology 136(6):1945–1949.

Gaffney, E.V. et al. (1987) "Quantitation of human interleukin–1β with polyclonal antibodies" Journal of Immunological Methods 101:271–277.

Gery, I., B. Waksman (1972) "Potentiation of the T–Lymphocyte Response to Mitogens" The Journal of Experimental Medicine 136:143–155.

Gubler, U. et al. (1986) "Recombinant Human Interleukin 1α: Purification and Biological Characterization" The Journal of Immunology 136(7):2492–2497.

Hanson, Y. et al. (1987) "A rapid method for detection of cellular proliferation using carboxyfluorescein" Journal of Immunological Methods 100:261–267.

Johnstone, A., R. Thorpe (1987) "Immunoadsorption and purification of antibodies" Immunochemistry in Practice, Second Edition, p. 218.

Kaye, J. et al. (1984) "Growth of a cloned helper T cell line induced by a monoclonal antibody specific for the antigen receptor: interleukin 1 is required for the expression of receptors for interleukin 2" J. Immunol 133:1339–1345.

Kenney, J.S. et al. (1987) "Monoclonal Antibodies to Human Recombinant Interleukin 1 (IL 1)β: Quantitation of IL 1β and Inhibition of Biological Activity" The Journal of Immunology 138(12):4236–4242.

Köck, A. et al. (1986) "Characterization of a Monoclonal Antibody Directed Against the Biologically Active Site of Human Interleukin 1" J. Exp. Med. 163:463–468.

(List continued on next page.)

Primary Examiner—Toni R. Scheiner
Attorney, Agent, or Firm—Saliwanchik, Lloyd & Saliwanchik

[57] ABSTRACT

The subject invention concerns a novel selective, sensitive, and highly reliable immunoassay for detecting human IL-1β in cultured mononuclear cells or human body fluids. It is a sandwich immunoassay which is useful in diagnostic work to detect IL-1β selectively, for the first time, from among similar lymphokines and other substances known to interfere with bioassays for IL-1.

14 Claims, 6 Drawing Sheets

OTHER PUBLICATIONS

Kunkel, S.L., S.W. Chensue (1985) "Arachidonic Acid Metabolites Regulate Interleukin–1 Production" Biochemical and Biophysical Research Communication 128(2):892–897.

Limjuco, G. et al. (1986) "Antibodies of predetermined specificity to the major charged species of human interleukin 1" Proc. Natl. Acad. Sci. USA 83:3972–3976.

Lomedico, P.T. et al. (1987) "Cloning and Expression of Murine, Human, and Rabbit Interleukin 1 Genes" Lymphokines 13:139–150.

Lomedico, P.T. et al. (1984) "Cloning and expression of murine interleukin–1 cDNA in *Escherichia coli*" Nature 312:458–462.

March, C.J. et al. (1985) "Cloning, sequence and expression of two distinct human interleukin–1 complementary DNAs" Nature 315:641–647.

Luger, T.A. et al. (1987) "Monoclonal anti–IL 1 is directed against a common site of human IL 1α and IL 1β" Chemical Abstracts 106:31167, abstract No. 31168x.

Peck, R. et al. (1987) "The production and characterization of anti–interleukin–1 monoclonal antibodies" Lymphokine Research 6(1):abstract No. 1102.

Lo, R.J. et al. (1987) "An $IgG_1$ Monoclonal Antibody to IL–1β" Lymphokine Research 6(1):abstract No. 1103.

Censini, S. et al. (1987) "Antibodies to Human Interleukin 1 Beta" Lymphokine Research 6(1):abstract No. 1113.

Conlon, P.J. et al. (1987) "Localization of Interleukin (IL–1) in Monokine Producing Cells by Monoclonal Antibodies to IL–1α and OI–1β" Lymphokine Research 6(1):abstract No. 1117.

Dinarello, C.A. et al. (1977) "Human leukocytic pyrogen: Purification and development of a radioimmunoassay" Proc. Natl. Acad. Sci. USA 74(10):4624–4627.

Rosenwasser, L.J. et al. (1981) "Ability of Human Leukocytic Pyrogen to Enhance Phytohemagglutinin Induced Murine Thymocyte Proliferation" Cellular Immunology 63:134–142.

Kronheim, S.R. et al. (1985) "Human Interleukin 1—Purification to Homogeneity" J. Exp. Med. 161:490–502.

Cahill, J. and K.E. Hopper (1984) "Immunoregulation by Macrophages III Prostaglandin E Suppresses Lymphocyte Activation but not Macrophage Effector Function During *Salmonella enteritidus* Infection" Int. J. Immunopharmac. 6(1);9–17.

SELECTIVE IMMUNOASSAY FOR IL-1β

CROSS-REFERENCE TO RELATED APPLICATIONS

This application is a division of application Ser. No. 08/164,283, filed Dec. 7, 1993 now U.S. Pat. No. 5,474,899; which is a continuation of application Ser. No. 07/958,442, filed Oct. 6, 1992, now abandoned; which is a continuation of application Ser. No. 07/496,168, filed Mar. 19, 1990, now abandoned, which is a continuation of application Ser. No. 07/049,630, filed May 13, 1987, now abandoned.

BACKGROUND OF THE INVENTION

Interleukin-1 (IL-1) is important to the activation of T and B lymphocytes and mediates many inflammatory processes. cDNAs coding for two distinct forms of IL-1 have been isolated and expressed; these cDNAs represent two different gene products, termed I1-1β (Auron, P. E., Webb, A. C., Rosenwasser, L. J., Mucci, S. F., Rich, A., Wolff, S. M. and Dinarello, C. A. |1984| Proc. Natl. Acad. Sci. USA 81:7909) and IL-1α (Lomedico, P. T., Gubler, U., Hellman, C. P., Dukovich, M., Giri, J. G., Pan, Y. E., Collier, K., Semionow, R., Chua, A. O. and Mizel, S. B. |1984| Nature 312:458). IL-1β is the predominant form produced by human monocytes both at the mRNA and protein level. The two forms of human IL-1 share only 26% amino acid homology. Despite their distinct polypeptide sequences, the two forms of IL-1 have structural similarities (Auron, P. E., Rosenwasser, L. J., Matsushima, K., Copeland, T., Dinarello, C. A., Oppenheim, J. J. and Webb, A. C. |1985| J. Mol. Cell Immunol. 2:169), in that the amino acid homology is confined to discrete regions of the IL-1 molecule. The two forms of IL-1 also possess identical biological properties, including induction of fever, slow wave sleep, and neutrophilia, T- and B-lymphocyte activation, fibroblast proliferation, cytotoxicity for certain cells, induction of collagenases, synthesis of hepatic acute phase proteins, and increased production of colony stimulating factors and collagen. IL-1 also activates endothelial cells, resulting in increased leukocyte adhesiveness, $PGI_2$ and $PGE_2$ (prostaglandins) release, and synthesis of platelet activating factor, procoagulant activity, and a plasminogen activator inhibitor. Clearly, IL-1 plays a central role in local and systemic host responses. Because many of the biological effects of IL-1 are produced at picomolar (pg) concentrations in vivo, IL-1 production is likely a fundamental characteristic of host defense mechanisms.

In view of the multiple biological properties of IL-1 associated with inflammation and catabolic processes, the consequences of high levels of IL-1 in localized tissues such as bone and articular spaces are major concerns in the management and treatment of inflammatory diseases. Considerable attention has focused, therefore, on understanding the mechanisms of IL-1 production, and the precise function of IL-1 activity in inflammation. There are, then, two main areas of interest: measurement of IL-1 in body fluids and production of IL-1 from cells in vitro. At present, measurement of IL-1 produced in in vivo or in vitro is dependent on bioassays. T-cell assays for IL-1, based on the production of lnterleukin-2 (IL-2) or increased responsiveness to IL-2, are highly sensitive and can detect 10–100 pg/ml of IL-1 (Dinarello, C. A., Cannon, J. G., Mier, J. W., Bernheim, H. A., LoPreste, G., Lynn, D. L., Love, R. N., Webb, A. C., Auron, P. E., Reuben, R. C., Rich, A., Wolff, S. M. and Putney, S. D. |1986| J. Clin. Invest. 77:1734). However, these assays are vulnerable to interferences by several substances, including other lymphokines, such as IL-2 and IL-4 that directly stimulate T-cell division (Fox, D., Schlossman, S. and Reinherz, E. |1986| J. Immunol. 136:1945). The responses of endothelial (Bevilacqua, M. P., Pober, J. S., Majeau, G. R., Cotran, R. S. and Gimbrone, M. A. Jr. |1984| J. Exp. Med. 160:618; Dejana, E., Balconi, G., De Castellarnau, C., Barbieri, B., Vergara-Dauden, M. and de Gaetano, G. |1983| Biochim. Biophys. Acta 750:261) and synovial cells (Dayer, J-M, de Rochemonteix, Burrus, B., Demczuk, S. and Dinarello, C. A. |1986| J. Clin. Invest. 77:645) can be used to measure IL-1; some of these assays are adequately sensitive. But, these and other non-T-cell assays are not specific for IL-1 since the measured responses are also observed with other macrophage products, including tumor necrosis factor (Dinarello, C. A., Cannon, J. G., Wolff, S. M., Bernheim, H. A., Beutler, B., Cerami, A., Figari, I. S., Palladino, M. A. Jr. and O'Connor, J. V. |1986| J. Exp. Med. 163:1433; Beutler, B. and Cerami, A. |1986| Nature 320:584).

The measurement of IL-1 present in the supernates from cultured cells in vitro can be effected by the transfer into the IL-1 assays of substances used to either stimulate or suppress IL-1 production. For example, mitogens and adjuvants interfere with T-cell assays, while endotoxins and other bacterial products often mimic IL-1 activities in vivo. Several pharmacological agents which inhibit IL-1 production also interfere with biological assays for IL-1 (Dinarello, C. A., Marnoy, S. O. and Rosenwasser, L. J. |1983| J. Immunol. 130:890). Separating such agents from IL-1 can be difficult since most of these substances bind to protein. Prostaglandins and other arachidonic acid metabolites are also produced in cell cultures during stimulation of IL-1 production and their presence during IL-1 bioassays can either inhibit (Cahill, J. and Hopper, K. E. |1984| Int. J. Immunopharmacol. 6:9) or enhance (Kunkel, S. L. and Chensue, S. W. |1985| Biochem. Biophys. Res. Commun. 128:892) IL-1 activity. Monocytes themselves also produce polypeptide substances that have been shown to inhibit IL-1 activity in several assays (Arend, W. P., Joslin, F. G. and Massoni, R. J. |1985| J. Immunol. 134: 3868). All of these factors show that the determination of IL-1 activity is not a straightforward process or a predictable process. Thus, there is a need in the art for a selective and predictable assay for determining the level of IL-1β in human fluids, e.g., serum or urine.

The most widely employed IL-1 bioassay is the thymocyte co-stimulator or mouse lymphocyte activating factor (LAF) assay (Gery, I. and Waksman, B. H. |1972| J. Exp. Med. 136:143). The results of this assay are known to vary with the health and age of the mouse and the presence of thymic and accessory epithelial cells. Although the murine cloned T-helper cell line, D10.G4.1 exhibits remarkable sensitivity to IL-1 (Kaye, J., Gillis, S., Mizel, S. B., Shevach, E. M., Malek, T. R., Dinarello, C. A., Lachman, L. B. and Janeway, C. A. Jr. |1984| J. Immunol. 133:1339), these assays are also vulnerable to the presence of interfering substances "carried-over" from cell supernates or body fluids. Moreover, the response of these cells to IL-1 is often inconsistent between testing laboratories. The inconsistencies may be due to the requirement for macrophage feeder cells, growth factors and/or culture conditions. Some IL-1 T-cell assays involve a 2-step procedure whereby supernates are transferred to another cell line in order to measure IL-2 levels (Conlon, P. J. |1983| J. Immunol. 131:1280); this procedure is vulnerable to the presence of IL-2 in the original sample. The immunoassay described herein for IL-1β offers the advantage, for the first time, of establishing standard methods for measuring IL-1β and reducing the differences which occur because of different responding cells or individual laboratory practices.

BRIEF SUMMARY OF THE INVENTION

The subject invention concerns a selective, sensitive, and highly reliable immunoassay for detecting human IL-1β in cultured mononuclear cells or human body fluids. Specifically, the invention is a competitive immunoassay for human IL-1β which is, advantageously, monospecific. More specifically, the invention is exemplified by use of a radioimmunoassay (RIA) which detects 250 pg/ml of IL-1β. This assay can be used to measure IL-1β in a variety of cell supernates which contain substances which interfere with in vitro and/or in vivo IL-1. Further, the invention assay selectively detects IL-1β in the presence of human serum or urine. The novel IL-1β immunoassay of the invention comprises (a) labeling of recombinant human IL-1β (rIL-1β) to obtain labeled human rIL-1β;

(b) separating labeled rIL-1β and free label;

(c) analyzing the peak labeled fraction for binding with excess anti-rIL-1β antibody; and (d) using the fractions with both the highest specific binding and the lowest non-specific binding in a competitive immunoassay to determine the level of human IL-1β in cultured mononuclear cells or human body fluids.

The RIA exemplified herein (Chart A) uses a radioactive isotope, usually I-125, to label a known antigen—here, recombinant human IL-1β. This labeled antigen (Ag*) competes with the target non-labeled antigen of a specimen for the binding site of a given amount of "monospecific" antibody (Ab). The radioactivity of the Ag*-Ab complex inversely indicates the amount of non-radioactive Ag-Ab complexes in the system, and therefore the amount of the target Ag of the specimen.

This subject competitive inhibition assay, which uses labeled IL-1β, and polyclonal rabbit antisera produced to recombinant human IL-1β, detects, in an RIA assay, 25 pg/ml of recombinant human IL-1β and 50 pg/ml of pI 7 human monocyte IL-1. Advantageously, the assay does not detect human IL-1α, human interleukin-2, human tumor necrosis factor-α, or human interferon-γ. Nearly 100% of IL-1 added to human serum or urine can be quantitatively recovered. Substances such as fetal calf serum, phytohemagglutinin, opsonized *Staphylococcus albus* or *E. coli* endotoxin do not affect the assay. Using this assay, human monocyte IL-1β was measured in both the intracellular and extracellular compartments and the results were unaffected by indomethacin or BW 755C, a lipoxygenase inhibitor. The assay also detected crude human monocyte IL-1β in supernatants from endotoxin challenged mononuclear cells. The utility of the subject process is clearly evident in quantitating human IL-1β in biological fluids and detection of IL-1 in the presence of other lymphokines. Further, the sensitivity and specificity of the subject assay permits the detection of IL-1β in a variety of tissue culture supernates. The assay detects IL-1β in the presence of PHA (phytohemagglutinin) or endotoxin, substances known to interfere with bioassays for IL-1. PHA can affect T-cell assays by the induction of IL-2 production while endotoxin mimics IL-1 in a variety of in vivo as well as in vitro assays.

Figure 1:
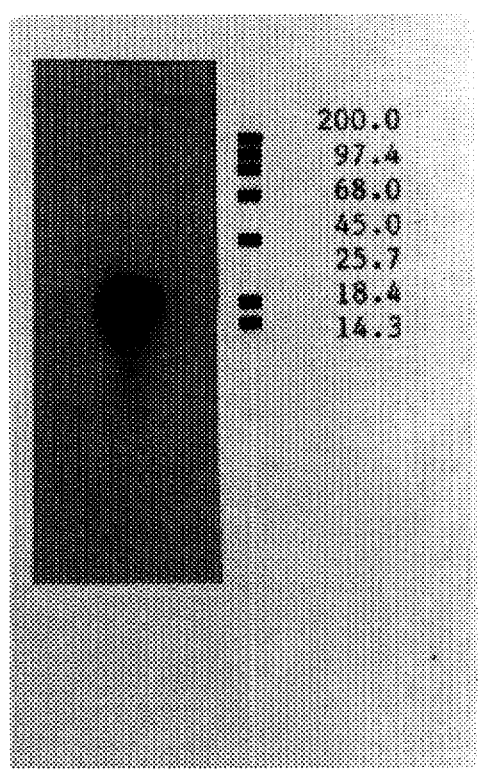
FIG. 1: SDS-PAGE of $^{125}$I-labeled IL-1β. The positions of the various molecular weight markers is indicated.

The supernate was concentrated (20-fold) in 3.5 KD dialysis tubing against PEG (6–8,000) and applied to a 30×1.0 cm column. The column was eluted in RPMI and each fraction was assayed directly in the RIA and after a 1:250 and 1:500 dilution, assayed for biological activity in D10.G4.1 cells ((Kaye et al. supra).

DETAILED DISCLOSURE OF THE INVENTION

Following are examples which illustrate procedures for practicing the invention. These examples should not be construed as limiting. All percentages are by weight and all solvent mixture proportions are by volume unless otherwise noted.

Example 1—Recombinant human IL-1β and production of rabbit antisera

The recombinant IL-1β protein was expressed in *E. coli* and the 17,000 dalton peptide was produced by endoproteolytic cleavage, representing the 152 amino acid carboxy terminal portion of the 31 kD precursor molecule (Auron, P. E., Webb, A. C., Rosenwasser, L. J., Mucci, S. F., Rich, A., Wolff, S. M. and Dinarello, C. A. [1984] Proc. Natl. Acad. Sci. USA 81:7909; Dinarello, C. A., Cannon, J. G., Mier, J. W., Bernheim, H. A., LoPreste, G., Lynn, D. L., Love, R. N., Webb, A. C., Auron, P. E., Reuben, R. C., Rich, A., Wolff, S. M. and Putney S. D. [1986] J. Clin. Invest. 77:1734). Antibodies to rIL-1β were elicited in New Zealand white rabbits by the intradermal injection of 100 μg rIL-1β in complete Freund's adjuvant on day 0. On day 40 the animals received a subcutaneous booster injection of 25 pg in incomplete Freund's adjuvant. A second, third and fourth booster injection followed on day 50, day 106 and day 189. The animals were bled on day 203 for use of the sera in the radioimmunoassay. This antiserum specifically neutralized human IL-1β when tested in either T-cell (Kaye et al. supra) or endogenous pyrogen assays (Dinarello et al. [1986] J. Clin. Invest. 77:1734). When tested against recombinant-human IL-1α, no neutralizing effect was observed in either T-cell or endogenous pyrogen assays.

Example 2—Iodination and purification of labeled rIL-1β rIL-1β was iodinated to a specific activity of 15 uCi/μg by a modification of the Chloramine T method (Hunter, W. M. and Greenwood, F. C. [1962] Nature 194:495). To about 10 μg of rIL-1β (435 μg/ml) in about 0.5M sodium phosphate buffer, pH 7.4, was added about 0.5 mCi Na $^{125}$I (100 mCi/ml, Amersham Corporation, Arlington Heights, Ill.); about ten μg chloramine T (2.5 mg/ml, Kodak, Rochester, N.Y.) in 0.5M sodium phosphate buffer, pH 7.4 was added to the mixture. The mixture was manually shaken for about 10 sec; about 100 μg sodium metabisulfite (5.0 mg/ml) in about 0.5M sodium phosphate buffer pH 7.4 was added to stop the reaction. The loss of $^{125}$I-IL-1β on the walls of the vials was prevented by adding about 0.3 ml of 0.2% BSA (Sigma, St. Louis, Mo.) in about 0.01M phosphate buffered saline, pH 7.4. Immediately after the iodination procedure, the mixture was applied to a 0.6×30 cm column of G-25 SEPHADEX (Pharmacia, Piscataway, N.J.) previously equilibrated in about 0.2% BSA (Sigma) in about 0.01M phosphate buffered saline (pH 7.4). The $^{125}$I-rIL-1β and free $^{125}$I were separated on the column with the same buffer. An aliquot of each 0.5 ml fraction was counted in a gamma spectrometer. The peak radioactive fractions were analyzed for binding with excess anti-rIL-1β antibody; Eighty to ninety per cent of the iodinated protein was bound by excess anti-IL-1β antibody while less than 8% was bound by normal rabbit serum (non-specific binding). The fractions with both the highest specific binding and the lowest non-specific binding were used in the radioimmunoassay. FIG. 1 illustrates the purity of the $^{125}$I-labeled IL-1β following sodium dodecyl sulfate polyacrylamide gel electrophoresis (SDS PAGE) (Laemmli, V. K. [1970] Nature (Lond.) 277:680).

Example 3—Radioimmunoassay

All assays were performed in duplicate in 12×75 mm polystyrene tubes. Both simultaneous and sequential assays were used. In the simultaneous assay, about 0.1 ml of a rIL-1β standard in normal human serum, tissue culture media (RPMI 1640) or 0.2% BSA, about 0.15M sodium chloride, about 0.01M sodium phosphate buffer, pH 7.4 (assay buffer) was added to each tube. Fifty μl of $^{125}$I-rIL-1β in assay buffer containing 4% normal rabbit serum were added followed by about 0.1 ml rabbit anti-rIL-1β serum diluted appropriately in the assay buffer. The tubes were shaken and allowed to incubate for about 18 hr at about room temperature (23° C.)

The sequential assay differed from the simultaneous assay in that the $^{125}$I-rIL-1β was added about 18 hr after the rIL-1β standard and antiserum were mixed; the mixture was then incubated for an additional 24 hr at about room temperature (23° C.). In both assays the separation of antibody bound from free $^{125}$I-rIL-1β was accomplished by the addition of about 1.0 ml 6% polyethylene glycol (mol wt—8000) in about 0.001M sodium phosphate buffer (pH 7.4) containing about 2.5% sheep anti-rabbit IgG serum (Pel-Freez, Rogers, AR). The tubes were agitated, centrifuged at 1000× g for 15 min at room temperature; the supernatants were removed by aspiration, and the precipitates counted in an automated gamma spectrometer for about 1 min. Non-specific binding was determined by substituting normal rabbit serum at a corresponding dilution in place of the antiserum.

Example 4—Human cell supernates

Blood from normal human subjects was separated on FICOLL-HYPAQUE (Pharmacia) and mononuclear cells (MNC) were suspended in Eagle's minimal essential medium containing 100 μg/ml streptomycin, 100 U/ml penicillin, 0.01M 4-(2-hydroxyethyl)-1-piperazine ethane- sulfonic acid (HEPES) buffer (all from Microbiological Associates, Walkersville, Md.) at a concentration of about 5×10$^6$ cells/ml. Heat-inactivated AB serum was added to a final concentration of about 1%. One hundred μl of the cell suspension was added to flat bottom microtiter wells (Nunc, Rotskilde, Denmark) and 100 μl of either control medium or medium containing various substances were added. After about 24 hr of incubation at about 37° C., the supernates were removed. The cells were then frozen (about −70° C.) in about 200 μl of fresh culture medium. Three freeze-thaw cycles were used to extract the intracellular material; the lysate was then centrifuged at about 10,000× g for about 5 min at 4° C. All extracellular and intracellular materials were frozen at about −70° C. until they were assayed.

Example 5—IL-1 bioassays

Murine thymocytes and a subclone of the murine T-cell line D10.G4.1 (Kaye et al. supra) were used to assay IL-1. The D10.G4.1 cells are from about 50–100 times more sensitive to stimulation by IL-1 than are thymocytes (Kaye et al. supra). The rabbit endogenous pyrogen assay was used as previously described (Dinarello, C. A. [1986] J. Clin. Invest. 77:1734).

Following are examples illustrating the use of the invention process:

Example 6

Figure 5:
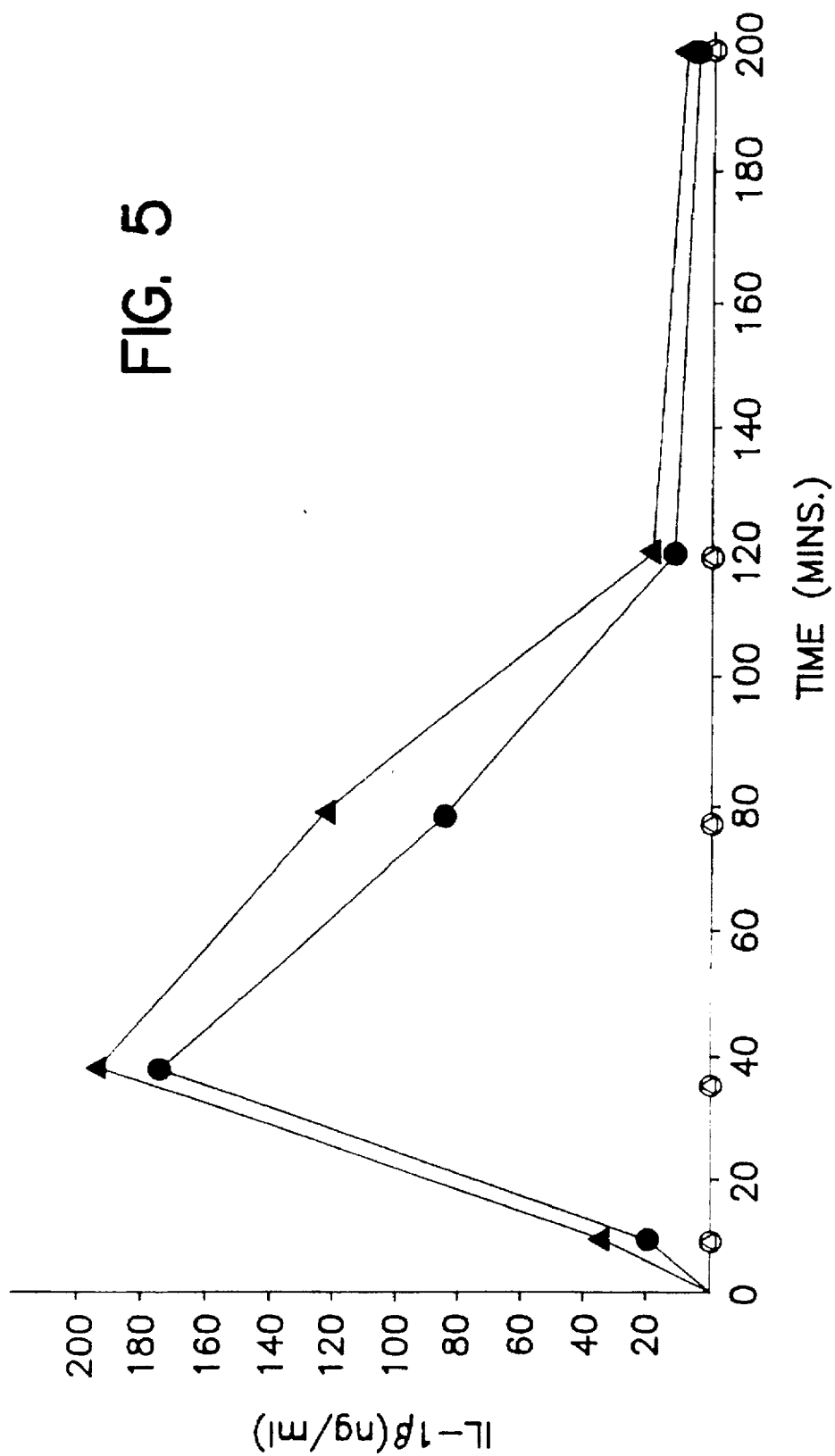
FIG. 5: IL-1β circulating life in C3H/HeJ mice as determined by the IL-1β radioimmunoassay following an intraperitoneal injection of recombinant IL-1β. Following a sham injection or the injection of IL-1β the mice were bled at the indicated time intervals and the heparinized plasma assayed for IL-1β. 2 mice in each group. Mice injected with buffer (○—○), (Δ—Δ). Mice injected with 100 μg IL-1β (●—●), (▲—▲).

To determine the utility of the invention process in measuring actual clinical samples, tests were made of plasma from mice injected intraperitoneally with rIL-1α. The rIL-1β detected in the circulation of these mice is shown in FIG. 5. For this experiment, the rIL-1β standards were diluted in fresh frozen normal mouse plasma. These and the results in Table I demonstrate the usefulness of this assay for the determination of rIL-1β levels following parenteral injection.

Example 7

The invention process also can be used to detect IL-1β produced in human mononuclear cells stimulated with endotoxin, opsonized Staphylococcus albus, or PHA. In addition, agents such as indomethacin or BW 755C (Dinarello et al., 1983, supra), which interfere with T-cell proliferation assays do not interfere with the invention process. The effects of both stimulatory substances as well as inhibitory factors in the bioassays for IL-1 can be overcome by the use of the invention process see Table II.

Example 8—Use of the invention process to detect various molecular weight fragments of IL-1β

Figure 6:
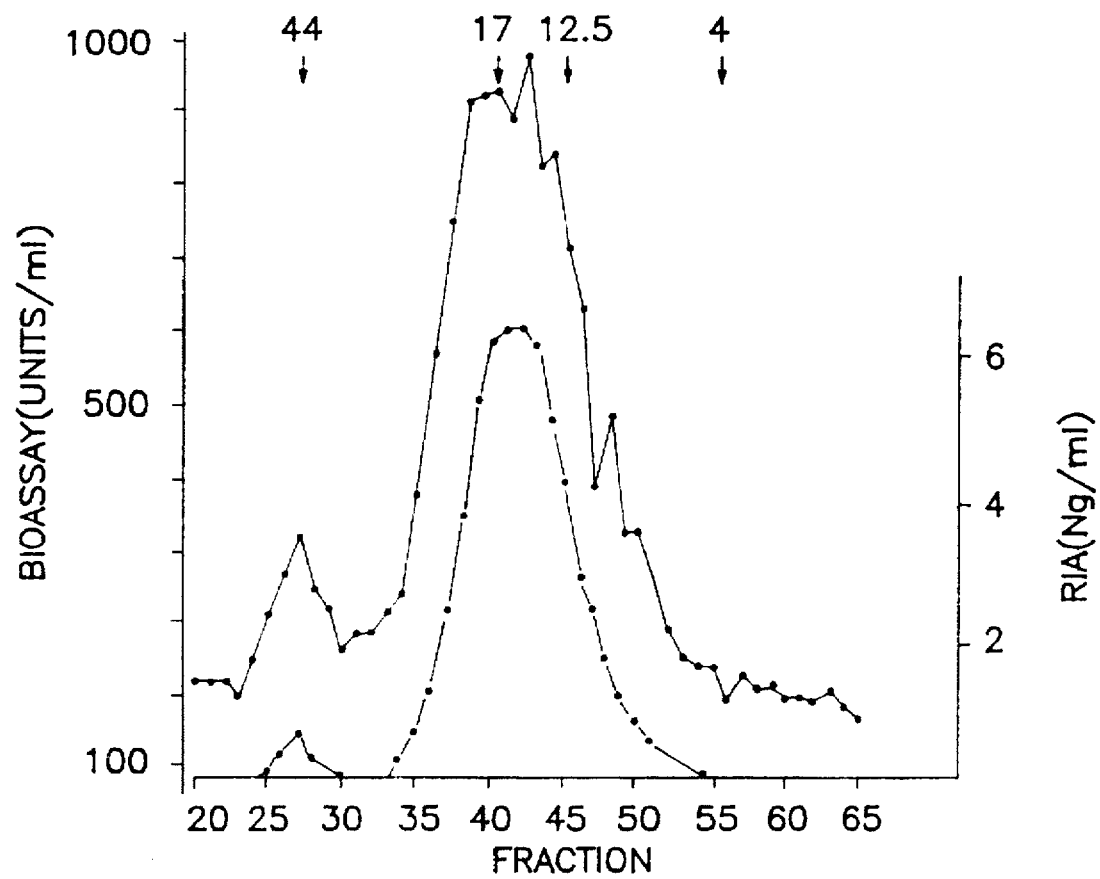
FIG. 6: G-50 gel filtration chromatography of human MNC (mononuclear cells) supernates stimulated with heat-killed *Staphylococcus albus* (Dinarello, C. A., Clowes, G. H. A. Jr., Gordon, A. H., Saravis, C. A. and Wolff, S. M. [1984] J. Immunol. 133:1332).

Several molecular sizes of IL-1β have been described using various biological assays. There are data that suggest the large molecular weight IL-1's are less potent in various bioassays. Since the process of the subject invention detects IL-1β as antigen rather than as a biologically active molecule, the quantitation of IL-1β at various molecular weights, in different cell compartments and under conditions of protease inhibition can be determined (Lepe-Zuniga, J. L., Zigler, J. S. Jr., Zimmerman, M. L. and Gery, I [1985] Mol. Immunol. 22: 1387). IL-1 from adherent human blood monocytes stimulated with opsonized *Staphylococcus albus* (Dinarello, C. A., Bendtzen, K. and Wolff, S. M. [1982] Inflammation 6:63) was chromatographed over SEPHADEX G-50 (Pharmacia) and each fraction was assayed for biological activity on D10.G4.1 cells and in the invention process. The results illustrated in FIG. 6 indicate that the invention process can be used to detect IL-1 with a variety of molecular weights.

In performing the invention assay using the above materials and methods, the following results were obtained:

(1) Binding of $^{125}$I-rIL-1β to anti-IL-1β

Figure 2:
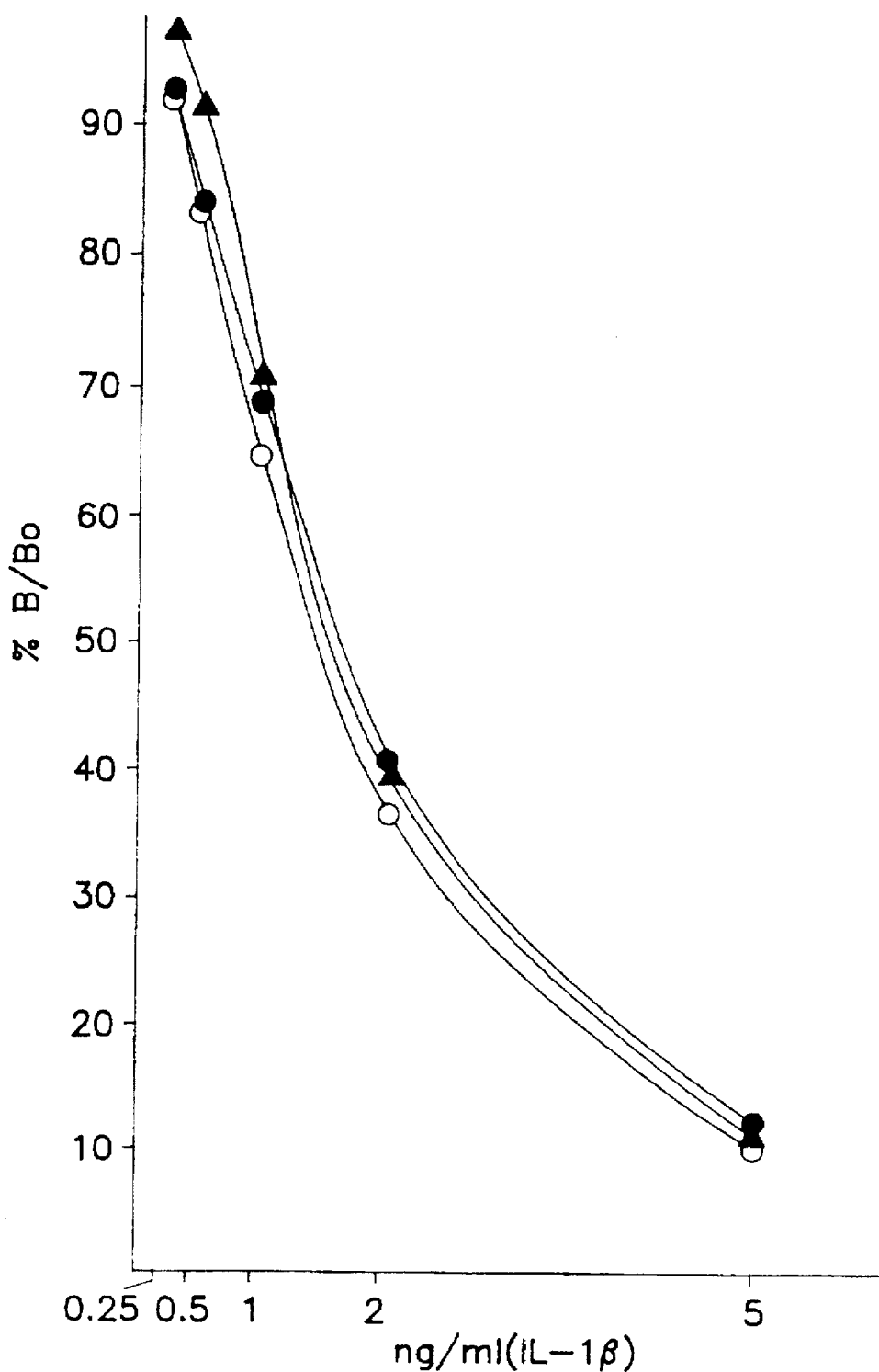
FIG. 2: Standard curves for the IL-1β radioimmunoassay with IL-1β standards diluted in heat inactivated normal human sera (▲—▲), 0.2% BSA in 0.01M phosphate buffered saline (pH 7.5) (○—○) and RPMI 1640 with 5% FCS (heat inactivated) (●—●).

A comparison of the binding inhibition curves obtained when the rIL-1β standards are diluted in assay buffer, culture medium (RMPI 1640) and serum is shown in FIG. 2. The curves derived using the sequential assay procedure were virtually super-imposable. For the most accurate determination of the quantity of IL-1β the rIL-1β standards were diluted in the same medium as the unknown samples.

Figure 3:
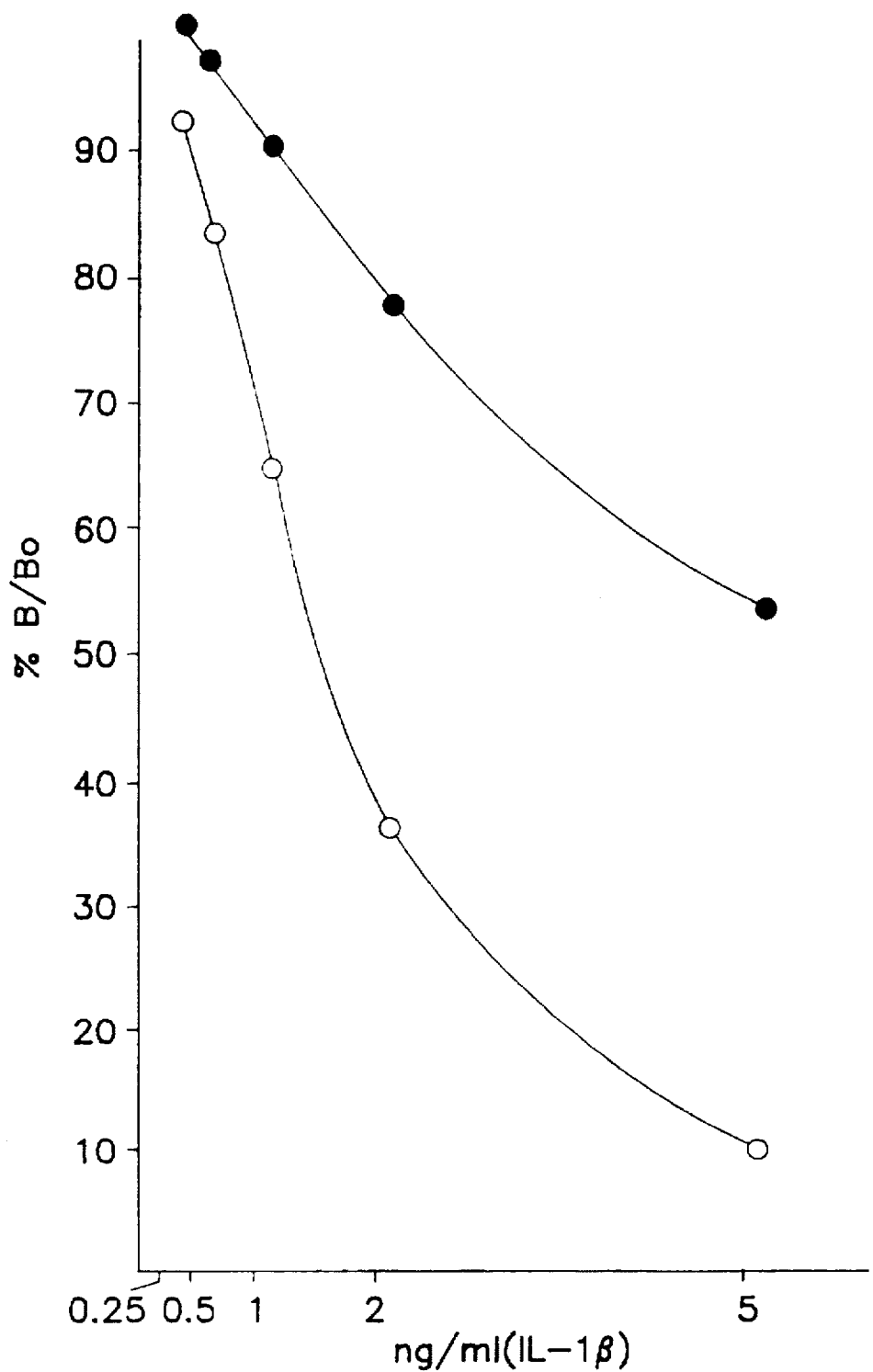
FIG. 3: Standard curves for the IL-1β radioimmunoassay with immediate (○—○) and delayed (●—●) addition of $^{125}$I-IL-1β. The lower limit of detection for IL-1β was 25 pg with a delayed addition of 125I-IL-1β and 75 pg with an immediate addition.

FIG. 3 shows the binding inhibition curves obtained using the human serum based standards in both the simultaneous and sequential assays. A substantial displacement of labeled rIL-1β occurred when more than 25 pg rIL-1β was added in the sequential assay, while a similar displacement was observed at IL-1β levels greater than 75 pg in the simultaneous assay.

(2) Specificity of RIA for human IL-1β

The antiserum used in the assay was shown to be specific for rIL-1β in that it lacked cross reactivity with rIL-1α (100 ng/ml), rIL-2 (200 ng/ml), rTNFα (50 µg/ml), and IFNγ ($1\times10^6$ u/ml) (Table I). Shown in Table I is the nearly complete recovery of IL-1 when added to and incubated with fresh frozen human serum and urine. Human serum and urine are known to contain inhibitory substances that prevent the detection of IL-1 in most in vitro biological assays unless separated from the IL-1.

Figure 4:
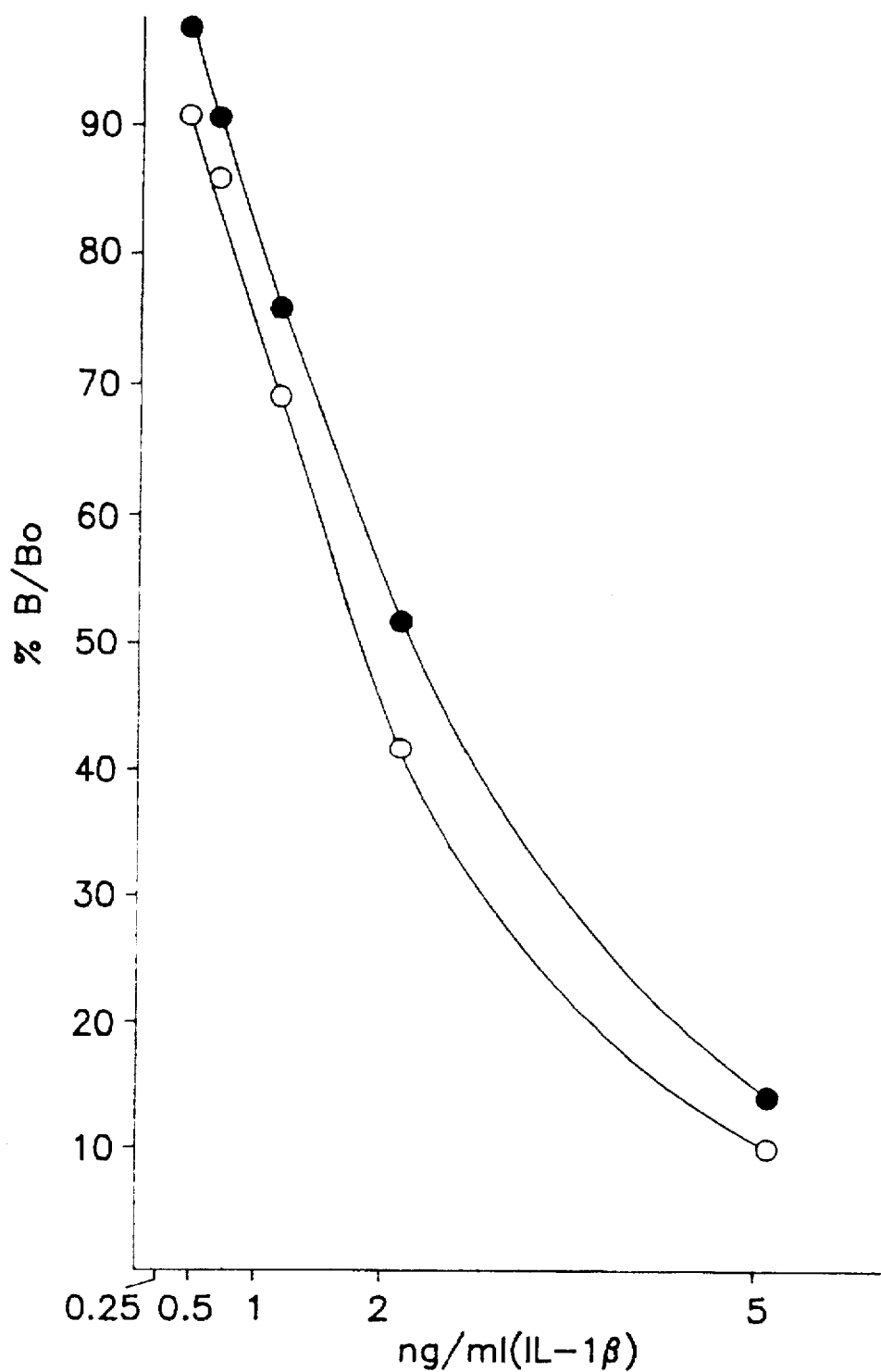
FIG. 4: Standard curves for the IL-1β radioimmunoassay with recombinant IL-1β (○—○) and monocyte-derived IL-1 (pI 7) (●—●) as standards diluted in 0.2% BSA in 0.01M phosphate buffered saline (pH 7.5). No cross reactivity was apparent with IL-1α (100 ng/ml) (Genzyme, Boston, Mass.), tumor necrosis factor-α (50 ng/ml) (gift of Genentech), gamma interferon (1×10$^5$ u/ml) or IL-2 (200 ng/ml) (Genzyme) (data not shown).

Using the thymocyte co-mitogenesis assay, ten half maximal units/ml of purified monocyte IL-1 (pI 7) and recombinant IL-1β gave a displacement equal to 0.4 ng/m-L and 1.0 ng/ml rIL-1β, respectively. These results reflect the differences in specific activity of the two IL-1 preparations (purified monocyte-derived IL-1 [$2.5\times10^7$ U/mg] and rIL-1β [$1\times10^6$ U/mg])(Dinarello et al. [1986] J. Clin. Invest. 77:1734). FIG. 4 compares the competitive inhibition curves of rIL-1β and purified monocyte IL-1, pI 7, in the RIA.

The invention assay, described above, can be carried out using alternative procedures. These other embodiments of the invention are as follows:

1. Radiolabel IL-1β with $^{125}$I via the $^{125}$I-Bolton-Hunter reagent (Bolton, A. E. and Hunter, W. M. [1973] Biochem. J. 133:529–539). Use I-IL-1β as described in Example 2.
2. Immobilize anti-IL-1β on a solid support. Label IL-1β with an enzyme or fluorogenic material. Use these reagents in a competitive binding assay.
3. Immobilize rabbit anti-IL-1β on a solid support. Label rabbit anti-IL-1 with an enzyme or fluorogenic material. Use these reagents to "sandwich" IL-1β present in sample.
4. Immobilize mouse monoclonal anti-IL-1β on a solid support. Label rabbit anti-IL-1β with an enzyme or fluorogenic material. Use the reagents to "sandwich" IL-1β present in sample.
5. Immobilize mouse monoclonal anti-IL-1β on a solid support. "Sandwich" IL-1β present in sample with rabbit anti-IL-1β. Add radioisotope, enzyme or fluorogenic material labeled anti rabbit IgG to detect rabbit anti-IL-1β. This signal is proportional to the amount of IL-1β. This assay, known as the enzyme linked immunosorbent assay (ELISA) can be carried out as follows:

100 µl of a monoclonal antibody specific for IL-1β appropriately diluted in 0.01M sodium phosphate buffer, pH 7.4 was passively adsorbed to a polystyrene microtiter plate. The plate was washed with 0.01M phosphate buffer, pH 7.4 containing 0.05% Tween-20 after an overnight incubation at 23° C. The plate was subsequently overcoated with 0.01M sodium phosphate buffer, pH 7.4 containing 1% bovine serum albumin (BSA). The plate was incubated for 2 hr at 23° C. and washed as described above.

100 µl of a serum, urine culture medium or buffer containing IL-1β solution was added to the wells of the plate. The plate was incubated for 2 hr at 37° C. The plate was washed as described above. One hundred µl of rabbit anti IL-1β serum appropriately diluted in 0.01M sodium phosphate, 0.15M sodium chloride, pH 7.4, containing 0.2% BSA was added to each well and incubated for 2 hr at 37° C. The plate was washed as described above. 100 µl of a goat anti rabbit IgG-horseradish peroxidase conjugate (Pel Freez, Rogers, Ak.) appropriately diluted in assay buffer was added to each well and incubated for 30 min at 37° C. The plate was washed as described above.

To develop the color, 100 µl of o-phenylene diamine (0.4 mg/ml) in citrate-phosphate buffer, pH 5.0, containing 0.01% $H_2O_2$ was added to each well. The reaction is stopped by the addition of 50 µl of 4N $H_2SO_4$ and the plate read in a microtiter plate reader at O.D.$_{410}$.

The quantity of IL-1β in the unknown sample is determined from a standard curve constructed using known quantities of IL-1β, for example, as follows:

| IL-1β (ng/ml) | O. D.$_{410}$ |
| --- | --- |
| 0.000 | 0.119 |
| 0.016 | 0.160 |
| 0.031 | 0.195 |
| 0.063 | 0.243 |
| 0.125 | 0.331 |
| 0.250 | 0.492 |
| 0.500 | 0.750 |
| 1.000 | 1.055 |

A kit for the above assay would contain the following:
(1) a microtiter plate with monoclonal antibody specific for IL-1β absorbed to the wells;
(2) a container of rabbit anti IL-1β antibody;
(3) a container of goat anti rabbit IgG-horseradish peroxidase conjugate;
(4) a container with interleukin-1β standard;
(5) a tablet of o-phenylenediamine;
(6) a container of $H_2O_2$;
(7) a container of 4N $H_2SO_4$; and
(8) a container of wash buffer.

The use of these alternative procedures in the subject invention process is well within the skill of a person in the art. No undue experimentation would be involved to achieve essentially the same advantageous results as disclosed above. Further, it should be recognized that, once the subject concept of the invention is known, it is well within the skill of persons in the art to employ this concept with other modifications and achieve essentially the same advantageous results as disclosed herein. Thus, this invention includes not only the specific procedures disclosed herein but also all modifications of these procedures which give essentially the same results.

A wide variety of solid phase supports can be used to immobilize the anti-IL-1β. For example, suitable supports are dextran and cellulose, and continuous surfaces such as polystyrene and polypropylene discs, or the walls of plastic or glass tubes or slides. Plastic surfaces exhibit adsorptive properties, and simply exposing such surface to an appropriate dilution of the antibody will lead to the attachment of a proportion of the antibody molecules thereon. The bond is probably ionic or hydrophobic, and not covalent. Covalent bonding, however, can be readily obtained by the incorporation of cross-linking agents such as glutaraldehyde and other agents in the antibody solution used for the coating.

Coated tube systems offer great convenience in the actual performance of assays and the technique can be widely used in commercial kits.

The anti-IL-1β can be labeled with a radioactive material such as $^{125}$iodine, as disclosed herein; labeled with an optical label, such as a fluorescent material; or labeled with an enzyme such as horseradish peroxidase. The anti-IL1β also can be biotinylated and labeled avidin used to detect its binding to the immunoadsorbent.

After incubation with the labeled antibody, the immunoadsorbent is separated from the solution and the label associated with the immunoadsorbent is evaluated. Depending upon the choice of label, the evaluation can be done in a variety of ways. The label can be detected by a gamma counter if the label is a radioactive gamma emitter, or by a fluorimeter, if the label is a fluorescent material. In the case of an enzyme, label detection may be done calorimetrically, employing a substrate for the enzyme.

For convenience and standardization, reagents for the performance of the assay can be assembled in assay kits. A kit for screening body fluids, for example, serum, can include:

(1) a container with interleukin-1β antiserum;

(2) a container with labeled interleukin-1β, for example, $^{125}$I interleukin-1β; and, (3) a container with interleukin-1β standard.

A kit also will contain a buffer containing bovine serum albumin (BSA), and polyethylene glycol in separate containers.

An example of a kit for 100 assay tubes including standard curves is as follows:

1 vial interleukin-1β antiserum; lyophilized; 10 ml after reconstitution. Rabbit interleukin-1β antiserum in buffered saline containing bovine serum albumin. Contains 0.1% sodium azide as a preservative.

1 vial $^{125}$I interleukin-1β; lyophilized; 10 ml after reconstitution. Radioactively labeled interleukin-1β in buffered saline containing rabbit serum and bovine serum albumin. Contains 0.1% sodium azide as a preservative. 5 uCi.

1 vial interleukin-1β standard; lyophilized; 0.5 ml after reconstitution. 50 ng/ml interleukin-1β in buffered saline containing bovine serum albumin. Contains 0.1% sodium azide as a preservative.

1 bottle BSA phosphate buffer; 100 ml; phosphate buffered saline containing bovine serum albumin. Contains 0.1% sodium azide as a preservative.

1 bottle Polyethylene Glycol (PEG) Second Antibody; 100 ml; polyethylene glycol 6000 in phosphate buffer containing anit-rabbit IgG serum. Contains 0.1% sodium azide as preservative.

The reagent preparation for the above kit is as follows:

A. Interleukin-1β antiserum. Reconstitute with 10 ml distilled or deionized water. Swirl gently to insure that lyophilized reagent on the sides of vial is dissolved. Allow 10 to 15 min for reconstitution.

B. $^{125}$I-Interleukin-1β. Reconstitute with 10 ml distilled or deionized water. Swirl gently to insure that lyophilized reagent on the sides of vial is dissolved. Allow 10 to 15 min for reconstitution.

C. Interleukin-1β standard. Reconstitute with 0.5 ml distilled or deionized water. Swirl gently to insure that lyophilized reagent on the sides of vial is dissolved. Allow 10 to 15 min for reconstitution. The solution contains 50 ng/ml of interleukin-1β. Do not attempt to store the diluted standards.

D. BSA phosphate buffer. The buffer, based in 0.01M phosphate pH 7.0 with 0.2% bovine serum albumin containing 0.1% sodium azide, is supplied ready for use.

E. Polyethylene Glycol (PEG) Second Antibody. This suspension is supplied ready for use. Mix well before using.

The preparation of standards for the above kit is as follows:

The stock solution contains 50 ng/ml. Distribute serial dilutions of the stock standard concentrate into a series of test tubes to achieve the desired concentrations (suggested range: 5 ng/ml to 0.25 ng/ml) by dilution with the medium, serum or BSA phosphate buffer diluent supplied with the kit.* A reasonable dilution scheme is shown below. Prepare standards shortly before use; do not store diluted standards.

5.0 ng/ml—0.1 ml stock plus 0.9 ml buffer
2.0 ng/ml—0.4 ml of 5.0 ng/ml standard plus 0.6 ml buffer
1.0 ng/ml—0.2 ml of 5.0 ng/ml standard plus 0.8 ml buffer
0.5 ng/ml—0.1 ml of 5.0 ng/ml standard plus 0.9 ml buffer
0.25 ng/ml—0.05 ml of 5.0 ng/ml standard plus 0.95 ml buffer

*Standards should be prepared in the same diluent as the test samples.

The assay procedure for the above kit, which should be read in its entirety before beginning the assay, is as follows:

1. Label test tubes for the six interleukin-1β standards, total count (TC) tubes, non-specific binding (NSB) tubes, test samples and appropriate controls. Standards, controls, TC and NSB tubes should be tested in duplicate.

2. Pipette 100 μl of each standard, control and test sample into the proper tube. The NSB tubes should receive the zero standard.

3. Add 100 μl of the interleukin-1β antiserum to each tube except the TC and NSB tubes. (Add 100 μl of buffer to the NSB tubes). Mix by vigorously shaking the test tube rack ten times or by vortex mixing each tube.

4. Allow tubes to stand for 16–24 hr at room temperature (20° C. to 30° C.).

5. Add 100 μl of the $^{125}$I-interleukin-1β to each tube, including the TC tubes. Set the TC tubes aside at room temperature (20° C. to 30° C.) until Steps 6 through 9 are completed. Mix by vigorously shaking the test tube rack ten times or by vortex mixing each tube.

6. Allow tubes to stand for 16–24 hr at room temperature (20° C. to 30° C.).

7. Add 1.0 ml PEG-Second Antibody Solution to each tube except the TC tubes. Mix thoroughly on a vortex-type mechanical mixer for 3 to 5 sec.

8. Centrifuge all tubes except the TC tubes at a minimum of 1000× g for 15 min. The tubes need not be centrifuged in a refrigerated centrifuge, although that is an acceptable option.

9. Aspirate or decant completely each tube, except the TC tubes, without disturbing the precipitate. If a decanting procedure is used, invert tubes with a smooth motion and gently blot against absorbent paper to remove residual droplets.

10. Place all tubes in a gamma counter. Determine the level of radioactivity in each tube. Extending the counting time generally improves the accuracy of gamma counter results.

Alternate assay procedure

For an overnight yet less sensitive assay, follow Steps 1, 2, and 3 in the assay procedure, omit Step 4, and follow steps 5 through 10. This procedure will yield an assay with a minimal detection limit of 1.0 ng/ml interleukin-1β.

The calculations and plotting for the above assay are as follows:

1. Calculate the average counts for each set of duplicate tubes.

2. Calculate the average net counts by subtracting the average of the NSB tubes.

3. Calculate the percent B/Bo for all standards and samples as follows:

$$\text{Percent } B/Bo = \frac{\text{counts standard or sample} - NSB \times 100}{\text{counts zero standard} - NSB}$$

4. Construct a standard curve by plotting the average percent bound for each standard on the vertical (Y) axis and the corresponding dose value on the horizontal (X) axis. Construct the curve of best fit through the points.
5. The amount of interleukin-1 in each sample is determined by interpolation from the standard curve.

Note: Samples with concentration greater than the range of the standard curve must be diluted in the appropriate solution and reassayed to determine the precise concentration of interleukin-1β.

Typical data for the above assay are as follows:

| Tube Number | Sample I. D. | CPM Minus Background | Avg. CPM | % B-NSB/T | % B/Bo |
|---|---|---|---|---|---|
| 1 | Total Counts (TC) | 19594 | 19514 | | |
| 1 | Total Counts (TC) | 19433 | | | |
| 2 | NSB | 760 | 738 | (4.0) | |
| 2 | NSB | 726 | | | |
| 3 | Zero Standard | 6845 | 6838 | 31.3 | |
| 3 | Zero Standard | 6831 | | | |
| 4 | 0.25 Standard | 6366 | 6323 | 28.6 | 91.3 |
| 4 | 0.25 Standard | 6281 | | | |
| 5 | 0.50 Standard | 5884 | 5879 | 26.3 | 84.0 |
| 5 | 0.50 Standard | 5875 | | | |
| 6 | 1.00 Standard | 5011 | 4965 | 21.7 | 69.3 |
| 6 | 1.00 Standard | 4920 | | | |
| 7 | 2.00 Standard | 3336 | 3220 | 13.2 | 42.2 |
| 7 | 2.00 Standard | 3305 | | | |
| 8 | 5.00 Standard | 1503 | 1517 | 4.0 | 12.8 |
| 8 | 5.00 Standard | 1531 | | | |

Performance characteristics of the above assay are as follows:

Sensitivity

The lowest concentration of interleukin-1β reproducibly detectable from the zero level (95% confidence) is 0.25 ng/ml.

Specificity

The antiserum used in this assay was shown to be specific for interleukin-1β. No cross reactivity was apparent with interleukin-1α, interleukin-2, tumor necrosis factor, or interferon-γ.

TABLE I

Recovery of rIL-1β Added to Human Serum and Urine

| Sample | Initial rIL-1β (ng/ml) | rIL-1β added (ng/ml) | rIL-1β measured (ng/ml) | Recovery (%) |
|---|---|---|---|---|
| Serum | | | | |
| #1 | 0 | 1.0 | 1.08 | 108 |
| #2 | 0 | 1.0 | 1.02 | 102 |
| #3 | 0 | 1.0 | 1.08 | 108 |
| #4 | 0 | 1.0 | 0.93 | 93 |
| #1 | 0 | 0.5 | 0.53 | 106 |
| #2 | 0 | 0.5 | 0.52 | 104 |

TABLE I-continued

Recovery of rIL-1β Added to Human Serum and Urine

| Sample | Initial rIL-1β (ng/ml) | rIL-1β added (ng/ml) | rIL-1β measured (ng/ml) | Recovery (%) |
|---|---|---|---|---|
| Urine | | | | |
| #1 | 0 | 1.0 | 1.13 | 113 |
| #2 | 0 | 1.0 | 1.17 | 117 |
| #1 | 0 | 1.45 | 1.35 | 93 |
| #2 | 0 | 1.45 | 1.43 | 99 |

TABLE II

Comparison of the Measurement of IL-1 from Cultured Mononuclear Cells

| Preparation | Bioassay (Units/ml IL-1) | Radioimmunoassay (ng/ml IL-1β) |
|---|---|---|
| Human MNC | | |
| unstimulated | 10 | <.2 |
| + ET 20 ng/ml | 175 | 9.8 |
| + ET 10 ng/ml | 150 | 9.7 |
| + ET 5 ng/ml | 160 | 8.5 |
| + ET 1 ng/ml | 170 | 4.2 |
| + PHA 30 ug/ml | 400 | 10.5 |
| + PHA 3 ug/ml | 300 | 7.8 |
| + Staph. albus | 150 | 35.0 |
| unstimulated | 0 | <0.2 |
| + ET 20 ng/ml | 150 | 14.0 |
| + ET 10 ng/ml | 150 | 15.0 |
| + ET 5 ng/ml | 160 | 12.0 |
| + PHA 30 ug/ml | 500 | 16.0 |
| + PHA 3 ug/ml | 400 | 3.5 |
| + Staph. albus | 200 | 50.0 |
| unstimulated | 20 | <0.2 |
| + ET 1 ng/ml | 120 | 2.4 |
| + ET 1 ng/ml + Indo* | 250 | 3.0 |
| + ET 1 ng/ml + BW755C** | 20 | 1.8 |
| unstimulated (intracell) | 0 | <0.2 |
| unstimulated (extracell) | 10 | <0.2 |
| + ET 1 ng/ml (intracell) | 80 | 2.4 |
| + ET 1 ng/ml (extracell) | 100 | 1.8 |
| unstimulated (intracell) | 10 | <0.2 |
| unstimulated (extracell) | 20 | <0.2 |
| + ET 10 ng/ml (intracell) | 220 | 0.3 |
| + ET 10 ng/ml (extracell) | 160 | 2.5 |

*1 uM
**10 uM

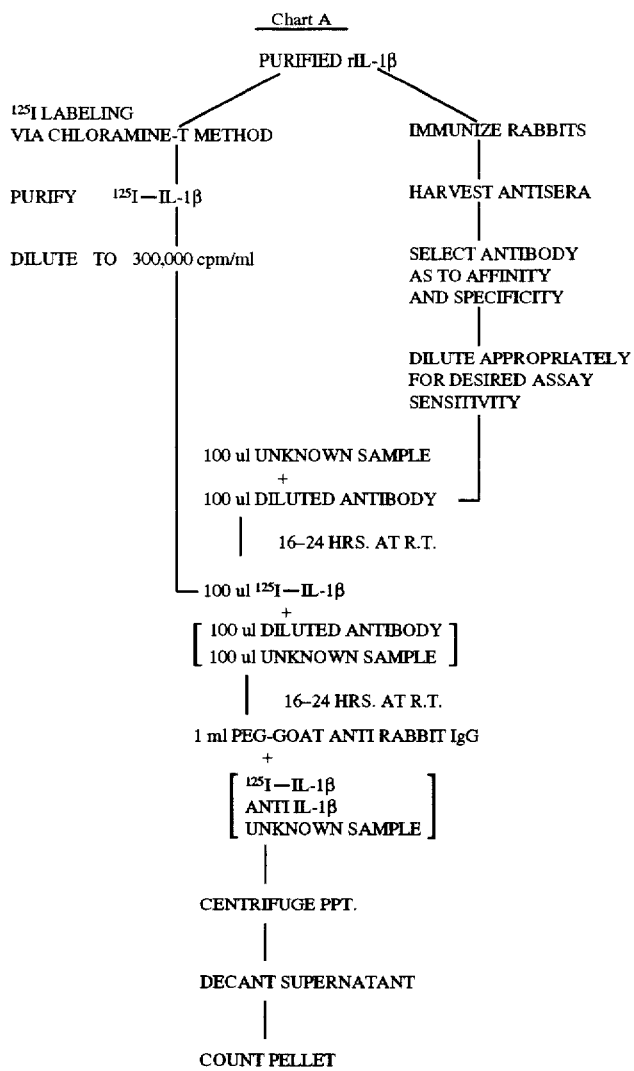

Chart A

NOTE: Volume of Reagents Ranging from About 25% to About 1,000% of Those Stated Above Can Be Used

I claim:

1. A method for detecting human interleukin-1β (IL-1β) in a sample, comprising contacting said sample with a first antibody that immunoreacts with IL-1β, wherein said first antibody is immobilized on a solid support and forms an immune complex with IL-1β in said sample, and contacting said immune complex with a second antibody that immunoreacts with IL-1β, and detecting said second antibody bound to said immune complex, wherein said second antibody is an antibody, or antigen-binding fragment thereof, that binds specifically to human IL-1β and does not bind to human IL-1α, human IL-2, human tumor necrosis factor-α, or human γ-interferon, and binds to human IL-1β in the presence or absence of phytohemagglutinin and endotoxin.

2. The method according to claim 1, wherein said first antibody is a monoclonal antibody.

3. The method according to claim 1, wherein said second antibody is a polyclonal antibody.

4. The method according to claim 1, wherein said second antibody is labelled with a detectable signal generating system, wherein a signal from said system is detectable.

5. The method according to claim 4, wherein said signal generating system is selected from the group consisting of radioisotopes, enzymes and fluorogenic compositions.

6. The method according to claim 1, wherein said second antibody bound to said immune complex is contacted with a moiety that binds to said second antibody, wherein said moiety is labelled with a detectable signal generating system, wherein a signal from said system is detectable.

7. The method according to claim 6, wherein said signal generating system is selected from the group consisting of radioisotopes, enzymes and fluorogenic compositions.

8. The method according to claim 1, wherein said solid support is selected from the group consisting of dextran, cellulose, plastic and glass.

9. The method according to claim 1, wherein said second antibody is biotinylated and said second antibody bound to said immune complex is contacted with avidin linked to a detectable signal generating system, wherein a signal from said system is detectable.

10. The method according to claim 9, wherein said signal generating system is selected from the group consisting of radioisotopes, enzymes and fluorogenic compositions.

11. A kit for performing an assay for detecting IL-1β in a sample, comprising in one or more containers:
   a) a first antibody that immunoreacts with IL-1β;
   b) a second antibody that immunoreacts with IL-1β wherein said second antibody is an antibody, or antigen-binding fragment thereof, that binds specifically to human IL-1β and does not bind to human IL-1α, human IL-2, human tumor necrosis factor-α, or human γ-interferon, and binds to human IL-1β in the presence or absence of phytohemagglutinin and endotoxin.

12. The kit according to claim 11, further comprising:
   c) an IL-1β standard.

13. The kit according to claim 11, wherein said first antibody is a monoclonal antibody.

14. The kit according to claim 11, wherein said second antibody is a polyclonal antibody.

* * * * *

UNITED STATES PATENT AND TRADEMARK OFFICE
CERTIFICATE OF CORRECTION

PATENT NO.   : 5,789,185
DATED        : August 4, 1998
INVENTOR(S)  : Peter J. Lisi It is certified that error appears in the above-identified patent and that said Letters Patent is hereby corrected as shown below:

Column 4, line 7: "125I-IL-1β" should read --$^{125}$I-IL-1β--;

line 14: "factor-a" should read --factor-α--;

line 58: "25 pg" should read --25 μg--; and line 65: "recombinant-" should read --recombinant--.

Column 6, line 28: "rIL-1α" should read --rIL-1β--.

Column 7, line 18: "IFNy" should read --IFNγ--;

line 27: "0.4 ng/m-L" should read --0.4 ng/ml--; and line 44: "anti-IL-1 with" should read --anti-IL-1β with--.

Column 9, line 14: "calorimetrically," should read --colorimetrically,--.

Column 11, line 9: "interleukin-1 in" should read --interleukin-1β in--.

UNITED STATES PATENT AND TRADEMARK OFFICE
CERTIFICATE OF CORRECTION

PATENT NO. : 5,789,185
DATED : August 4, 1998
INVENTOR(S) : Peter J. Lisi

It is certified that error appears in the above-identified patent and that said Letters Patent is hereby corrected as shown below:

Column 12, bottom of Table II:
    should read   --ET = endotoxin

--PHA = phytohemagglutinin

--Indo = Indomethacin

Column 13, bottom of Chart A: "NOTE: Volume" should read --NOTE: Volumes--.

Signed and Sealed this

Sixteenth Day of February, 1999

Attest:

Attesting Officer

*Acting Commissioner of Patents and Trademarks*